United States Patent
Neumann et al.

(10) Patent No.: US 6,451,307 B1
(45) Date of Patent: Sep. 17, 2002

(54) 3'-EXONUCLEASE, PRODUCTION AND USE THEREOF

(75) Inventors: Thomas Neumann, Frankfurt; Christoph Hüls, Wackernheim; Karl-Christian Gallert, Karben, all of (DE); Anders Virtanen, Uppsala (SE); Jonas Aström, Uppsala (SE); Javier Martinez, Uppsala (SE); Ann-Charlotte Thuresson, Uppsala (SE); Yanguo Ren, Uppsala (SE)

(73) Assignee: Aventis Research & Technologies GmbH & Co. KG, Frankfurt (DE)

( * ) Notice: Subject to any disclaimer, the term of this patent is extended or adjusted under 35 U.S.C. 154(b) by 0 days.

(21) Appl. No.: 09/719,787

(22) PCT Filed: Jun. 17, 1999

(86) PCT No.: PCT/EP99/04200

§ 371 (c)(1),
(2), (4) Date: Dec. 15, 2000

(87) PCT Pub. No.: WO00/00596

PCT Pub. Date: Jan. 6, 2000

(30) Foreign Application Priority Data

Jun. 29, 1998 (DE) ......................... 198 28 711

(51) Int. Cl.$^7$ .......................... A61K 38/46; C12N 9/22; C08H 1/00
(52) U.S. Cl. ....................... 424/94.6; 435/199; 530/412
(58) Field of Search .................. 435/199; 424/94.6; 530/412

(56) References Cited

PUBLICATIONS

Buiting K. et al, The human gene for the poly(A)–specific ribonuclease (PARN) maps to 16p13 and has a truncated copy in the Prader–Willi/Angelman syndrom region on 15q11fwdarwq13. Cytogenetics and Cell Genetics, (1999), 87, 125–131.*

Koerner C.G. et al, cDNA cloning of deadenylation nuclease (DAN): involvement in mRNA deadenylation during the meiotic maturation of Xenopusoocytes, EMBO J. 1998, 17, 5427–37.*

Köhler, G., et al, *Nature* 256:495–497, "Continuous cultures of fused cells secreting antibody of predefined specificity" (1975).

Schröder, H. C., et al, *J. of Biological Chem.* 255:4535–4538, "Purification and Characterization of a Poly (A)–specific Exoribonuclease from Calf Thymus" (1980).

Aström, J, et al, *J. of Biological Chem.* 267:18154–18159, "Properties of a HeLa Cell 3' Exonuclease Specific for Degrading Poly(A) Tails of Mammalian mRNA" (1992).

Körner, C. G., et al, *J. of Biological Chem.* 272:10448–10456, "Poly(A) Tail Shortening by a Mammalian Poly(A)–specific 3'–Exoribonuclease" (1997).

Virtanen, A., et al, *Progress in Molecular and Subcellular Biology 18:*199–220, "Function and Characterization of Poly(A)–Specific 3' Exoribonucleases" (1997).

* cited by examiner

*Primary Examiner*—Rebecca E. Prouty
*Assistant Examiner*—Malgorzata A Walicka
(74) *Attorney, Agent, or Firm*—Connolly Bove Lodge & Hutz LLP (57) ABSTRACT

The present invention relates to a poly(A)-specific 3'-exonuclease activity which can be obtained by chromatographically purifying a crude extract of animal or human cells and to its use for deadenylating 3'-poly(A) tails of nucleic acids and as a pharmaceutical or diagnostic agent, or for identifying functional interactors.

23 Claims, 6 Drawing Sheets

Poly(A) Sepharose fraction

3'-EXONUCLEASE, PRODUCTION AND USE THEREOF

DESCRIPTION

The present invention relates to a poly(A)-specific 3'-exonuclease activity which can be obtained by chromatographically purifying a crude extract of animal or human cells and to its use for deadenylating 3'-poly(A) tails of nucleic acids and as a pharmaceutical or diagnostic agent, or for identifying functional interactors.

Most eukaryotic mRNAs carry poly(A) tails of approx. 200 adenosine residues in length at their 3' ends. These poly(A) tails appear to influence not only the half-life or intracellular transport of mRNAs but also translation of the mRNA into the corresponding protein. While the precise mechanism has still not been elucidated, the synthesis and degradation of poly(A) tails appear to be directly or indirectly connected with the function of the tails (see, e.g., Wickens, M. et al. (1977) Curr. Opin. Genet. Dev., 7, 220–232).

Poly(A)-degrading nuclease activities have already been investigated in several eukaryotic systems (see, e.g., Virtanen, A. & Åström, J. (1997) in Prog. Mol. Subcell. Biol. (Jeanteur, P., ed.) Vol. 16, 199–220, Springer-Verlag, Berlin-Heidelberg). Thus, two reaction pathways have, for example, been identified in yeasts. One of the reaction pathways, i.e. the so-called deadenylation dependent decapping passway, is started by removal of the poly(A) tail and concerns a 5'-3'-exonucleolytic degradation of mRNA by an Xm1p5'-exonuclease. The other reaction pathway, i.e. the so-called 3'-5'-decay passway, is started by a deadenylation of the mRNA and concerns a 3'-5'-exoribonucleolytic degradation of mRNA. A multicomponent complex, termed an exosome, has recently been identified as being involved in the 3'-5'-decay passway (Mitchell, P. et al. (1997), Cell 91, 457–466). The exosome consists of several 3'-5'-exoribonucleases and is involved both in 5.8S rRNA 3' processing and in the 3'-5' degradation of mRNA (Anderson, J. S. J. & Parker, R. (1998) EMBO J. 17, 1497–1506). However, it is not known whether any of the exoribonucleases of the exosome degrade poly(A) preferentially. In addition to this, a poly(A)-binding protein I (PABI)-dependent poly(A)-specific nuclease (PAN) has been identified in yeasts (see, e.g., Lowell, J. E. et al. (1992) Genes Dev. 6, 2088–2099). PAN is a 3'-5'-exoribonuclease and is composed of at least two polypeptides, i.e. Pan2p and Pan3p (see, e.g., Brown, C. E. Jr. et al. (1996) Mol. Cell. Biol., 16, 5744–5753).

At least three different poly(A)-degrading activities have been characterized in mammalian cells. For example, an activity found in Hela cells has a high selectivity for degrading 3'-located poly(A) tails, requires 3'-located hydroxyl groups and forms 5'-AMP as the mononucleotide reaction product (see, e.g., Åström, J. et al. (1992) J. Biol. Chem. 267 (25), 18154–18159 and J. Aström, A. Aström and A. Virtanen, In vitro deadenylation of mammalian mRNA by a HeLa cell 3' exonuclease, EMBO J., (1991), Vol 10, 3067). Furthermore, an $Mg^{2+}$-dependent poly(A)-specific 3'-exoribonuclease having a molecular weight of 74 kDa (Körner, C. G. & Wahle, E. (1997) J. Biol. Chem., 272 (16), 10448–10456) has been described in calf thymus. A polyribosome-associated 3'-exoribonuclease having a molecular weight of 33 kDa has also been described, but this 3'-exoribonuclease is not specific for poly(A) (Caruccio, N. & Ross, J. (1994) J. Biol. Chem. 269 (50), 31814–31821). Another poly(A)-specific 3'-exonuclease activity having a molecular weight of 60 kDa was identified in calf thymus. However, it subsequently turned out that this protein is the hnRNP L protein and consequently has no connection with the poly(A)-specific 3'-exoribonuclease activity which has been measured.

The object of the present invention was therefore to make available a 3'-exoribonuclease which specifically degrades 3'-located poly(A) tails.

The present invention therefore relates to a process for isolating a poly(A)-specific 3'-exonuclease activity, which process contains the following steps:

a) preparing a crude extract from animal or human cells;

b) precipitating the protein present in the crude extract obtainable from step (a);

c) subjecting the precipitate obtainable from step (b) to chromatography on a basic anion exchanger;

d) subjecting the active fractions from step (c) to affinity chromatography;

e) subjecting the active fractions from step (d) to chromatography on a basic anion exchanger;

f) subjecting the active fractions from step (e) to affinity chromatography;

g) subjecting the active fractions from step (f) to poly (A)-affinity chromatography;

h) subjecting the active fractions from step (g) to chromatography on a basic anion exchanger; and, where appropriate, i) subjecting the active fractions from step (g) to gel filtration. Or j) subjecting the active fractions from step (f) to two rounds of affinity chromatography;

Surprisingly, the 3'-exonuclease activity which can be obtained by the above-described process is specific for 3'-located poly(A) tails, with a 3'-located hydroxyl group being required and with 5'-AMP being formed as the mononucleotide reaction product. In contrast to the already known 3'-exonuclease activities, the 3'-exonuclease activity according to the invention has a molecular weight of approx. 50 kDa under denaturing conditions. In contrast to the 74 kDa protein from calf thymus, the 3'-exonuclease activity according to the invention is not stimulated by spermidine at low salt concentrations; on the contrary, if anything, it is inhibited both at low and at high salt concentrations. Furthermore, in contrast to the calf thymus 74 kDa protein, the 3'-exonuclease according to the invention interacts relatively strongly with Heparin Sepharose. Furthermore, the calf thymus 74 kDa protein is not found in the SDS-Page—FIGS. 1B and 2B. In addition, it was surprising that, in contrast to the HeLa cell exonuclease activity, the exonuclease according to the invention is also active in the presence of $Mn^{2+}$. It is also surprising that the exonuclease according to the invention operates progressively, i.e. the exonuclease binds to the 3' end of the poly(A) tail and degrades it nucleotide by nucleotide without the exonuclease-poly(A) complex dissociating, whereas the 74 kDa protein operates distributively, with the complex dissociating after one operational step and having to be regenerated.

The poly(A)-specific 3'-exonuclease activity according to the invention can preferably be isolated from animal or human thymus cells, in particular from calf thymus. In general, a whole cell extract is prepared for this purpose, with protein preferably being precipitated from this extract with ammonium sulfate. In this connection, preference is given to the saturation concentration being approx. 45% ammonium sulfate. It has been found to be particularly advantageous in this connection if, before the true protein precipitation, foreign proteins are separated off by being precipitated at a saturation concentration of preferably approx. 25% ammonium sulfate, such that the desired 3'-exonuclease activity can, in a subsequent step, be precipitated out of the supernatant at an ammonium sulfate saturation of approx. 45%. This protein fractionation itself separates off a considerable portion of unwanted foreign proteins.

The precipitate is then subjected to chromatography on a basic anion exchanger, preferably on a weakly basic anion exchanger, in particular on DEAE, such as DEAE-Sepharose. In general, the active fraction elutes at an approx. 0.17 M concentration of a salt, preferably a monovalent salt such as KCl. The eluted active fraction, which has been dialyzed in a customary manner, is then subjected to an affinity chromatography, preferably on heparin, since it has been found, surprisingly, that the active fraction binds particularly well to heparin, e.g. Heparin Sepharose. The active fractions are therefore usually eluted at high salt concentrations, for example at an approx. 1.0 M concentration of a monovalent salt such as KCl. The active fractions are then subjected to chromatography on a basic anion exchanger, preferably on a strongly basic anion exchanger, in particular on Mono Q, such as Mono Q HR 16/10. The proteins are preferably eluted by means of a linear gradient, with it being possible to elute the active fractions at an approx. 10% concentration of a salt, in particular a monovalent salt such as KCl, whose concentration is approx. 1.0 M. After that, the active fractions are subjected to affinity chromatography, preferably on a dye, in particular on a blue dye, very particularly on Blue Sepharose. Preference is given to eluting the proteins using a multistep, in particular a two-step, salt gradient, with the active fractions preferably eluting well at a high salt concentration, in particular at high concentrations of a monovalent salt, very particularly at an approx. 1.0 M concentration, such as 1.0 M KCl.

According to the present invention, this is then followed by an affinity chromatography on poly(A), with it being possible to elute the active fractions at an approx. 0.35 to approx. 0.55 M concentration of a salt, in particular a monovalent salt, such as KCl. In addition, in conformity with the process according to the invention, the active fractions are subjected to chromatography on another basic anion exchanger, preferably on a strongly basic anion exchanger, in particular on Mono Q, such as SMART Mono Q. In this connection, the activity is preferably eluted at an approx. 0.17 M concentration of a salt, in particular a monovalent salt such as KCl. In conformity with the process according to the invention, the last purification step is, where appropriate, a step in which the active fractions are subjected to a gel filtration, preferably a Superdex 200 gel filtration, in particular a SMART Superdex 200 gel filtration, with it generally being possible to fractionate the active fractions satisfactorily in the presence of an approx. 0.1 M concentration of a salt, in particular a monovalent salt such as KCl.

In conformity with the process according to the invention, it is possible to purify a poly(A)-specific 3'-exonuclease activity approx. 600-fold with a yield of approx. 13% (see Table I). In this connection, it was particularly surprising that the poly(A) affinity chromatography in accordance with step (g) resulted in an approx. 14-fold purification of the activity according to the invention.

In another embodiment, the proteins are subjected, after the dye chromatography, to a double affinity chromatography, preferably chromatography on ssDNA Agarose followed by chromatography on 5'AMP Sepharose. The active fractions are normally eluted at high salt concentrations, such as an approx. 2.0 M concentration of a monovalent salt such as KCl.

The process according to the invention now results in the isolation of a poly(A)-specific 3'-exonuclease activity which runs at approx. 50 kDa under denaturing conditions, for example in an SDS-PAGE gel, and runs at from approx. 180 to 220 kDa under native conditions, for example on Superdex 200.

The invention therefore also relates to an approx. 50 kDa protein and, where appropriate, an associated protein (tetramer) which possesses a poly(A)-specific exonuclease activity and which can be obtained in accordance with the process according to the invention.

The present invention therefore also relates to a composition which comprises a poly(A)-specific 3'-exonuclease activity which can be obtained in accordance with the process according to the invention. Where appropriate, the composition comprises other additives and adjuvants.

The present invention also relates to a process for deadenylating nucleic acids, in particular for deadenylating 3'-located poly(A) tails belonging, preferably, to mRNA in the presence of a composition according to the invention. The deadenylation reaction preferably takes place in the presence of monovalent cations, such as $K^+$ and/or $Na^+$, in particular at concentrations of the monovalent cation of approx. 0.1 M. Preference is furthermore given to the deadenylation reaction taking place at a pH of approx. 7.

The present invention also relates to antibodies which react specifically with the composition according to the invention and/or a component thereof, with the composition itself being immunogenic or with it being possible to make the composition immunogenic, or to increase the immunogenicity of the composition, by coupling it to suitable carriers such as bovine serum albumin.

The antibodies are either polyclonal antibodies or monoclonal antibodies. Their preparation, which is also part of the subject matter of the present invention, is effected, for example in accordance with well-known methods, by immunizing a mammal, for example a rabbit, with the composition according to the invention, where appropriate in the presence of, for example, Freund's adjuvant and/or aluminum hydroxide gels (see, e.g., Diamond, B. A. et al. (1981) The New England Journal of Medicine, 1344). The polyclonal antibodies which are produced in the animal due to an immunological reaction can then readily be isolated from the blood in accordance with well-known methods and, for example, purified by means of column chromatography. Preference is given to purifying the antibodies by affinity chromatography, in which, for example, the composition according to the invention has been coupled to an NHS-activated HiTrap column.

Monoclonal antibodies can, for example, be prepared in accordance with the known method of Winter & Milstein (Winter, G. & Milstein, C. (1991) Nature, 349, 293).

The present invention furthermore also relates to a pharmaceutical which comprises a composition according to the invention and, where appropriate, suitable additives or adjuvants and to a process for producing a pharmaceutical for treating cancer, autoimmune diseases, in particular multiple sclerosis or rheumatoid arthritis, Alzheimer's disease, allergies, in particular neurodermatitis, type I allergies or type IV allergies, arthrosis, atherosclerosis, osteoporosis, acute and chronic infectious diseases and/or diabetis, and/or for influencing the metabolism of the cell, in particular in association with immunosuppression, very particularly in association with transplantations, in which pharmaceutical a composition according to the invention is formulated together with pharmaceutically acceptable additives and/or adjuvants.

Examples of suitable additives and/or adjuvants are a physiological sodium chloride solution, stabilizers, proteinase inhibitors, etc.

The present invention furthermore also relates to a diagnostic agent which comprises a composition according to the invention and, where appropriate, suitable additives and/or adjuvants and to a process for preparing a diagnostic agent for diagnosing cancer, autoimmune diseases, in particular multiple sclerosis or rheumatoid arthritis, Alzheimer's disease, allergies, in particular neurodermatitis, type I allergies or type IV allergies, arthrosis, atherosclerosis, osteoporosis, acute and chronic infectious diseases and/or diabetis, and/or for analyzing the metabolism of the cell, in particular the immune status, very particularly in association with transplantations, in which pharmaceutical suitable additives and/or adjuvants are added to a composition according to the invention.

For example, according to the present invention, the composition according to the invention can be bound to a solid phase, e.g. consisting of nitrocellulose or nylon, and in this way be brought into contact in vitro, for example, with the body fluid to be investigated, e.g. blood, in order thereby to be able to react, for example, with autoimmune antibodies. The antibody-peptide complex can then, for example, be detected using labeled antihuman IgG or antihuman IgM antibodies. The label is, for example, an enzyme, such as peroxidase, which catalyzes a color reaction. The presence of autoimmune antibodies, and the quantity of the antibodies which is present, can thereby be determined readily and rapidly by way of the color reaction.

Another diagnostic agent comprises the antibodies according to the invention themselves. Using these antibodies it is possible, for example, to readily and rapidly investigate a human tissue sample to determine whether the composition according to the invention and/or a component thereof is present. In this case, the antibodies according to the invention are labeled, for example, with an enzyme as has already been described above. This enables the specific antibody-peptide complex to be determined readily and just as rapidly by way of an enzymic color reaction.

The present invention also relates to a test for identifying functional interactors, such as inhibitors or stimulators, comprising a composition according to the invention or antibodies according to the invention and, where appropriate, suitable additives and/or adjuvants. For this, selected substances, for example from a so-called chemical library, are employed in the deadenylation reaction which has already been described in detail above and the activity of the composition according to the invention is measured in the presence and/or absence of the substances. An example of a suitable substrate is mRNA or poly(A). The test can be carried out, for example, in analogy with the in-vitro deadenylation, as described in detail in the examples.

Another general possibility of using the composition according to the invention is therefore also that of degrading nucleic acids, in particular mRNA, in a poly(A)-specific manner. The poly(A)-specific degradation of nucleic acids can be of particular use in research laboratories.

The following tables, figures and examples are intended to clarify the invention without limiting it.

DESCRIPTION OF THE TABLES AND FIGURES

Table 1 summarizes the purification of bovine poly(A)-specific 3'-exonuclease activity. The deadenylation activity was quantified by incubating the chromatographic fractions, under conditions for in-vitro deadenylation, with L3($A_{30}$) RNA substrate which had been labeled with [$\alpha^{32}$P]ATP during in-vitro transcription. One unit is defined as the release of 1 pmol of AMP per minute.

TABLE 1

| Fraction | Protein mg | Activity Units × $10^{-3}$ | Specific activity Units × $10^{-3}$/mg | Purification fold |
|---|---|---|---|---|
| A.S.45 | 65,280 | 72,000 | 1.1 | — |
| II | 3360 | 100,000 | 29.9 | 27 |
| IIB | 652 | 59,000 | 90 | 82 |
| MQ | 43.2 | 17,000 | 387 | 352 |
| C | 14.4 | 9,000 | 654 | 595 |

Table 2 shows the substrate specificity of the poly(A)-specific 3'-exonuclease activity.

TABLE II

| Substrate | Km(M) | Rel. Vmax/Km |
|---|---|---|
| poly(A) | 1 × $10^{-8}$ | 1 |
| poly(U) | 2 × $10^{-8}$ | 1/10 |
| poly(C) | 1 × $10^{-8}$ | 1/110 |
| poly(G) | 7 × $10^{-9}$ | 1/240 |

FIG. 1A shows the identification of the 50 kDa polypeptide by means of SMART Mono Q chromatography. In this connection, the Poly(A) Sepharose fraction was fractionated by SMART Mono Q chromatography and the resulting fractions were incubated, for 90 minutes, with uniformly labeled RNA substrate L3 ($A_{30}$) under in-vitro deadenylation conditions. The reaction products were fractionated by electrophoresis in a 10% polyacrylamide:bisacrylamide 19:1–7 M urea gel. The resulting fluorogram is depicted in FIG. 1A. Lane S denotes RNA substrate which is incubated in the absence of a fraction. Lane "Load MQ" denotes RNA substrate which is incubated with a Poly(A) Sepharose fraction. Lanes 6 to 18 denote RNA substrate which is incubated in the presence of the fractions which were obtained. Only even-numbered fractions were labeled.

FIG. 1B shows an SDS-PAGE of the SMART Mono Q fractions. In this case, aliquots of the fractions were separated by SDS-PAGE and the resulting gel was stained with silver. The fraction numbers are shown. Only even fractions were labeled. The molecular weight markers were separated in lane M. The numbers on the left-hand side indicate the molecular weights of the marker proteins in kDa.

FIG. 2A shows the identification of the 50 kDa polypeptide by means of SMART Superdex 200 chromatography. The resulting fractions were incubated, for 120 minutes, with uniformly labeled RNA substrate L3 ($A_{30}$) under in-vitro deadenylation conditions. The reaction products were fractionated on a 10% polyacrylamide:bisacrylamide 19:1–7 M urea gel. The resulting fluorogram is depicted in FIG. 2A. The L3 ($A_{30}$) lane shows the RNA substrate when incubated in the absence of a fraction. The Load lane shows the RNA substrate when incubated with Mono Q-concentrated Poly(A) Sepharose fraction. Lanes 15 to 25 show RNA substrate incubated in the presence of the resulting fractions. S and P indicate the migration sites of RNA substrate (S) and products (P). The elution profile of the molecular weight markers for calibrating the Superdex 200 column is depicted at the top.

FIG. 2B shows an SDS-PAGE of SMART Superdex 200 fractions. The resulting gel was stained with silver. The fraction numbers are shown. Only even fractions were labeled. The molecular weight markers were separated in lane M. The numbers on the left-hand side indicate the molecular weights of the marker proteins in kDa.

FIG. 2C shows the 5'AMP Sepharose 4B affinity fractionation of specific poly(A) exonuclease activity. Labeled fractions were incubated for 5 min with radioactive L3 (A30) RNA substrate. The reaction products were fractionated on a 10% polyacrylamide:bisacrylamide 19:1–7 M urea gel. The resulting fluorogram is depicted in FIG. 2C. In lane A, RNA substrate was incubated with 5'AMP Sepharose 4B affinity-purified exonuclease. In lane "-", the incubation was only with buffer in the absence of the active fraction.

FIG. 2D shows an SDS-PAGE of 5'-AMP affinity chromatography on Sepharose 4B. The resulting gel was stained with silver. The fraction numbers are indicated. Only even fractions were labeled. The molecular weight markers were separated in lane M. The numbers on the left-hand side indicate the molecular weights of the marker proteins in kDa.

FIG. 3 shows the specificity of the exonuclease for 3' end-located poly(A) tails. The Poly(A) Sepharose fractions were incubated, under in-vitro deadenylation conditions, with the RNA substrates L3 ($A_{30}$), L3 ($A_{30}$)$X_{15}$, L3($A_{30}$)$X_{49}$ and L3($A_{30}$)$X_{164}$, as indicated, for 0, 5, 10, 20, 30, 60 or 90 minutes, as indicated. The reaction products were fractionated in a 10% polyacrylamide:bisacrylamide 19:1–7 molar urea gel. The resulting fluorogram is shown in FIG. 3. S and P indicate the migration sites of the RNA substrates (S) and products (P).

FIG. 4 shows the 5'-AMP reaction product which is released during the deadenylation. The Poly(A) Sepharose fraction was incubated, for 20 minutes, under in-vitro deadenylation conditions, with L3($A_{30}$) RNA substrate which had been labeled with [$\alpha$-$^{32}$P]ATP during in-vitro transcription. 3 $\mu$l of the reaction mixture were subjected to a 2-D TLC. The resulting autoradiogram on the dried PEI cellulose plate is shown in FIG. 4. The migration sites of 2'-AMP, 3'-AMP and 5'-AMP markers, which were fractionated together with the radioactive sample, are indicated.

FIGS. 5A–C show the ongoing degradation of poly(A). The Poly(A) Sepharose fraction was incubated, under in-vitro deadenylation conditions, with X fmol of the L3($A_{30}$) RNA substrate which had been labeled with [$\alpha$-$^{32}$P] UTP during in-vitro transcription. The reaction products were fractionated in a 10% polyacrylamide:bisacrylamide 19:1–7 M urea gel. The resulting fluorogram is shown in FIGS. 5A–C. S and P indicate the migration sites of the RNA substrate (S) and the product (P). In this connection, FIG. 5A shows reactions which were carried out in the presence of 0.5 $\mu$l Poly(A) Sepharose fractions and terminated at the times indicated. FIG. 5B shows reactions which were carried out in the presence of 0.5 $\mu$l Poly(A) Sepharose fractions and terminated after 20 minutes. The indicated quantities of poly(A) in ng were added to the reactions. FIG. 5C shows reactions which were carried out in the presence of the indicated quantities of Poly(A) Sepharose fraction in $\mu$ and terminated after 20 minutes.

FIG. 6B:
Denaturing RNA polyacrylamide gel: The gel pieces obtained in FIG. 6A were eluted as described by Hager et al. The eluted proteins which were obtained were incubated with the L3($A_{30}$) substrate in accordance with Ex. 9 and the reaction mixtures were fractionated on a polyacrylamide gel. The activity was demonstrated to be present in gel piece C (approx. 50 kDa).

ABBREVIATIONS USED IN THE TEXT

L3: Poly(A) site in the late region of human adenovirus 2 (length: 54 nucleotides (J. Aström, A. Aström and A. Virtanen, In vitro deadenylation of mammalian mRNA by a HeLa cell 3' exonulease, EMBO, (1991), Vol 10, 3067)
$X_n$: n nucleotides (A,G,T,C)

EXAMPLES

Example 1
Preparing Cell-free Extracts

Crude whole-cell extracts were prepared from calf thymus in the manner described by Wahle, E. (1991) J. Biol. Chem. 266, 3131–3139. For this, from 3 to 15 kg of frozen calf thymus were thawed on ice, cut into pieces and homogenized, in an approximately equal quantity by volume of buffer 1 (50 mM Tris-HCl, 10 mM $K_3PO_4$, 1 mM EDTA, 10% glycerol, 50 mM KCl, 0.1 mM DTT, pH 7.9), in a Waring blender for 50 seconds at low speed and 50 seconds at high speed. The solid material was precipitated by centrifuging in a Sorwall GSA rotor at 16,000 g and 4° C. for 60 minutes. The crude extract was then filtered through a sieve having a mesh aperture of 7 (normal) (Pascal Eng. Co. Ltd.); 0.134 g of ammonium sulfate/ml (25% saturation) was then added and the extract was stirred on ice for 2 hours and the precipitate then precipitated by centrifuging in a Sorwall GSA rotor at 16,000 g and 4° C. for 60 minutes. A further 0.115 g of ammonium sulfate was then added per ml of supernatant (45% saturation) and the supernatant was then treated as already described above. The pellet which was obtained after the centrifugation was dissolved in from 2 to 4 volumes of buffer D (20 mM HEPES (KOH), 100 mM KCl, 1.5 mM $MgCl_2$, 0.2 mM EDTA, 0.5 mM DTT, 20% glycerol, pH 8.2) and this solution was dialyzed at 4° C. for 10 hours in a dialysis bag having a molecular weight exclusion limit of from 6000 to 8000. After the dialysis, the 45% ammonium sulfate fraction (A.S. 45) was frozen in liquid nitrogen and stored at −70° C. When 4.5 kg of calf thymus was used as the starting material, the A.S. 45 fraction (approx. 960 ml) then contained approx. 68 mg of protein per ml, giving a total quantity of protein of 65 g. The protein concentration was determined with a Biorad protein assay kit (No. 500-0001) using bovine gammaglobulin as the reference substance.

Example 2
Partially Purifying a Poly(A)-specific 3'-exonuclease Activity 960 ml of crude A.S. 45 fraction (65 g of protein) were used as the starting material for the partial purification (see Table I). Two essentially identical DEAE Sepharose chromatographies were carried out. In the first, 160 ml of the A.S. 45 extract were added to DEAE Sepharose CL-6B (Pharmacia No. 17-0710-01) ion exchanger (240 ml of matrix in the form of spheres) which had been equilibrated with buffer D. The suspension was stirred slowly at 4° C. for 30 minutes. Unbound material was removed by washing three times with buffer D and then centrifuging (Sorwall H 4000 rotor at 800 rpm for 3 minutes). The DEAE Sepharose matrix was then packed into a column (diameter 50 mm) and washed with buffer D at a flow rate of 9 cm per hour. A two-step salt gradient (buffer D containing 0.17 M and 1.0 M KCl, respectively) was carried out and the eluted protein was collected. The other 800 ml of the A.S. 45 fraction were fractionated in the same way. However, in this case, 240 ml of packed DEAE Sepharose were used and the column diameter was 70 mm. The protein which eluted at 0.17 M KCl, termed fraction II, was dialyzed against buffer D for 10 hours, frozen in liquid nitrogen and stored at −70° C. Subsequently, fraction II was fractionated by chromatography on Heparin Sepharose Cl-6B (Pharmacia No. 17-0467-01). The column, having a bed volume of 100 ml and a diameter of 50 mm, was equilibrated with buffer D at a flow rate of 9 cm per hour. Two essentially identical Heparin Sepharose fractionations were carried out. Fraction II (210 ml) was loaded onto a Heparin Sepharose Cl-6B column having a flow rate of 9 cm per hour. After the non-binding material had been eluted, bound protein was eluted by washing the column with buffer D containing 1.0 M KCl. The Heparin Sepharose column was used a second time in order to separate the remainder of fraction II (270 ml). The eluted fractions (termed IIB) were dialyzed, at 4° C., for 10 hours against buffer D, frozen in liquid nitrogen and stored at −70° C. Fraction IIB was then fractionated by means of four essentially identical FPLC (Pharmacia) chromatographies on Mono Q HR 16/10 (Pharmacia No. 17-0506-01). For this, a Mono Q column which had been equilibrated with buffer D was loaded with protein using a 50 ml Superloop (Pharmacia No. 19-7850-01) (approx. 30 ml of fraction IIB per cycle). The protein was eluted using a two-step linear gradient (0 to 20% 1.0 M KCl in 250 ml of buffer D and 20 to 50% 1.0 M KCl in 150 ml of buffer D), with 9 ml fractions being collected and the active fractions, which eluted at 10% 1.0 M KCl, being combined (termed fraction MQ), dialyzed at 4° C. for 10 hours against buffer D, frozen in liquid nitrogen and stored at −70° C. A 21 ml column packed with Blue Sepharose CL-6B (Pharmacia No. 17-0830-01) and having a diameter of 26 mm was prepared in accordance with the manufacturer's instructions. The column was equilibrated with buffer D at a flow rate of 34 cm per hour. The MQ fraction (108 ml) was loaded onto the column and bound protein was eluted using a two-step salt gradient (buffer D containing 0.17 M and 1.0 M KCl, respectively). The active fraction, termed C, which was obtained by eluting with 1.0 M KCl, was dialyzed at 4° C. for 10 hours against buffer D, frozen in liquid nitrogen and stored at −70° C.

Example 3
Poly(A) Sepharose Chromatography

Poly(A) Sepharose CL-6B was prepared in accordance with the manufacturer's instructions. An HR 10/10 column having a bed volume of 8 ml was equilibrated with buffer D containing 25 mM KCl at pH 7.12 mg (12 ml) of fraction C were dialyzed for 4 hours against 2×2 1 of buffer D containing 25 mM KCl at pH 7. The dialyzed fraction was loaded onto the column having a flow rate of 1 ml per minute. The column was then firstly washed with 5 bed volumes of buffer D containing 25 mM KCl at pH 7 and, after that, washed with 5 bed volumes of buffer D containing 200 mM KCl at pH 6 and, subsequently, with 5 bed volumes of buffer D containing 280 mM KCl at pH 6. A gradient (5 bed volumes) of from 280 to 600 mM KCl at pH 6 was then applied. The poly(A)-specific exonuclease activity eluted between 350 and 550 mM. This achieved a 14-fold purification of the nuclease activity.

Example 4
SMART Mono Q Chromatography

A SMART Mono Q PC 1.6/5 column was equilibrated with buffer D containing 50 mM KCl at pH 7 at a flow rate of 50 μl per minute. 1 ml of the Poly(A) Sepharose fraction (60 μg of protein) was dialyzed against buffer D containing 50 mM KCl at pH 7 and applied to the column at the same flow rate. The column was then loaded with a 1.5 ml gradient of from 50 to 500 mM KCl. 50 μl fractions were collected and the exonuclease activity was identified using an in-vitro deadenylation test (see below). The exonuclease activity eluted at approx. 170 mM KCl.

Example 5
SMART (Pharmacia, Uppsala) Superdex 200 Gel Filtration

The Poly(A) Sepharose fraction (0.7 ml, 0.06 mg per ml of protein) was firstly concentrated by means of a SMART Mono Q PC 1.6/5 (Pharmacia No. 17-0671-01) chromatography which was carried out in accordance with the following method. The column was equilibrated with buffer D containing 50 mM KCl at pH 7. The Poly(A) Sepharose fraction was dialyzed against buffer D containing 50 mM KCl at pH 7 and loaded onto a Mono Q column having a flow rate of 50 μl per minute. Bound material was eluted with a linear gradient of up to 500 mM KCl and 25 μl fractions were collected. The active fractions (total volume 100 μl) were identified and combined. 50 μl of the concentrated Poly(A) Sepharose fraction were then fractionated by gel filtration on a SMART Superdex 200 PC 3.2/30 column which had been equilibrated with buffer D containing 100 mM KCl at pH 7. The flow rate was 40 μl per minute. The active fractions were identified using an in-vitro deadenylation test (see below). The molecular weight markers were fractionated on a Superdex 200 column using the same method. The molecular weight markers were ferritin, catalase, aldolase and BSA having molecular weights of 440, 232, 158 and 67 kDa, respectively.

Example 6
ssDNA Agarose Affinity Chromatography ssDNA Agarose was prepared in accordance with the manufacturer's instructions (Pharmacia 27-5575-02). A 0.6 ml column was packed. The column was loaded with the active fraction C (10 ml) from Example 3 in buffer D containing 50 ml of KCl (pH 7.0). The run-through fraction was collected.

Example 7
5'-AMP Affinity Chromatography

5-AMP Sepharose (Pharmacia 17-0620-01) was prepared in accordance with the manufacturer's instructions and the run-through fraction from Example 6 was loaded onto the column in buffer D containing 50 ml of KCl (pH 7.0). The column was then washed with 5 ml of buffer D in 50 ml of KCl (pH 7.0). After that, it was washed with 5 ml of buffer D containing 200 ml of mM KCl (pH 7.0). Finally, the activity was eluted from the column with 2 ml of buffer D containing 2 M KCl (pH 7.0).

Figure 1A:
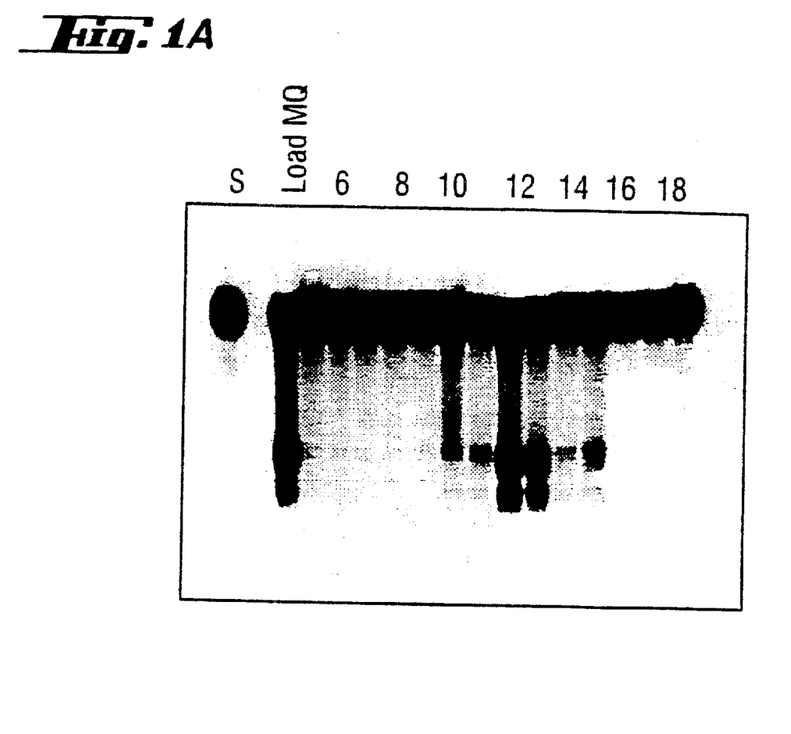
Figure 1B:
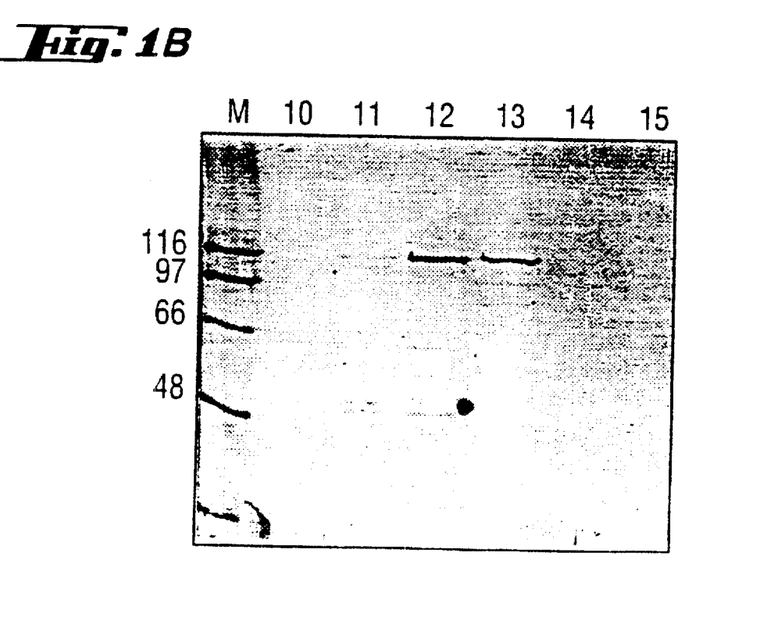
Figure 2A:
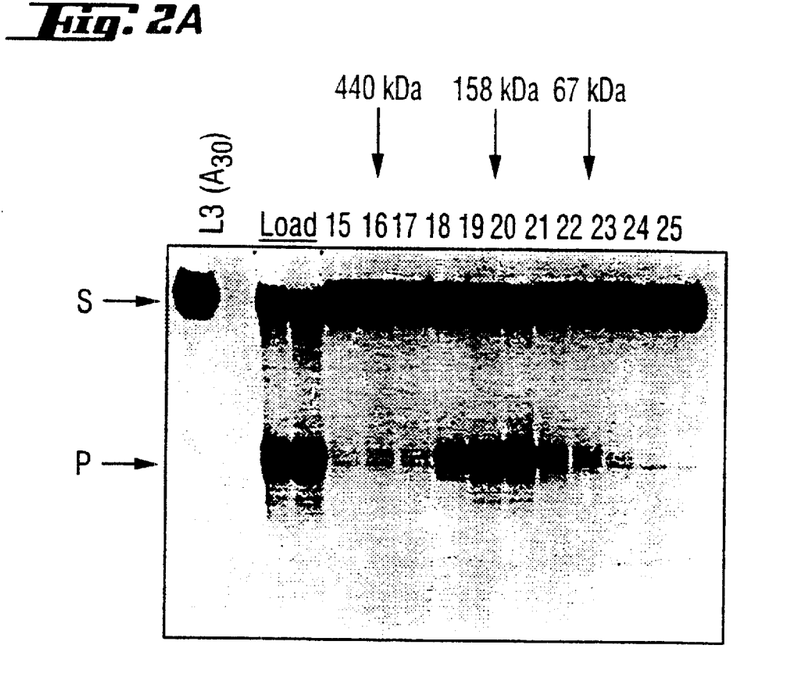
Figure 2B:
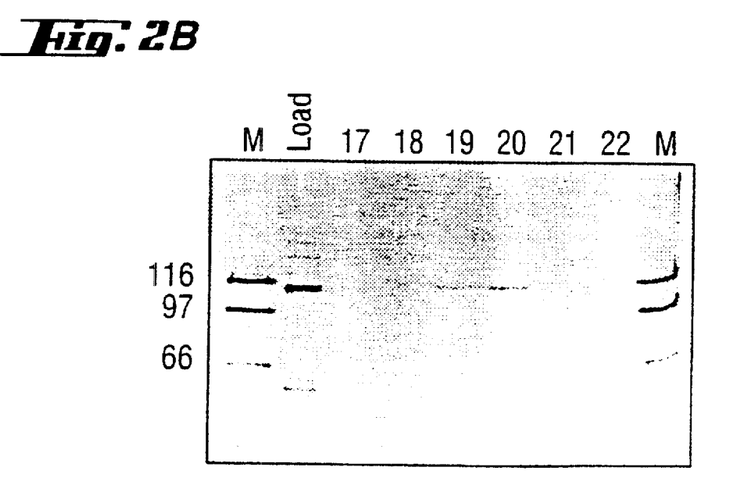
Figure 2C:
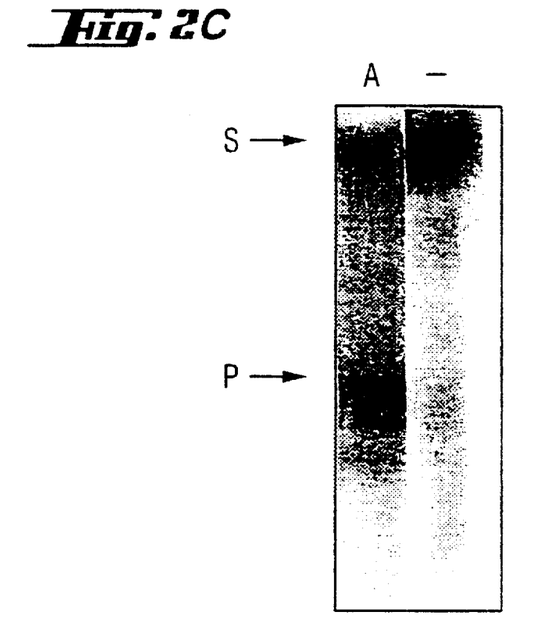
Figure 2D:
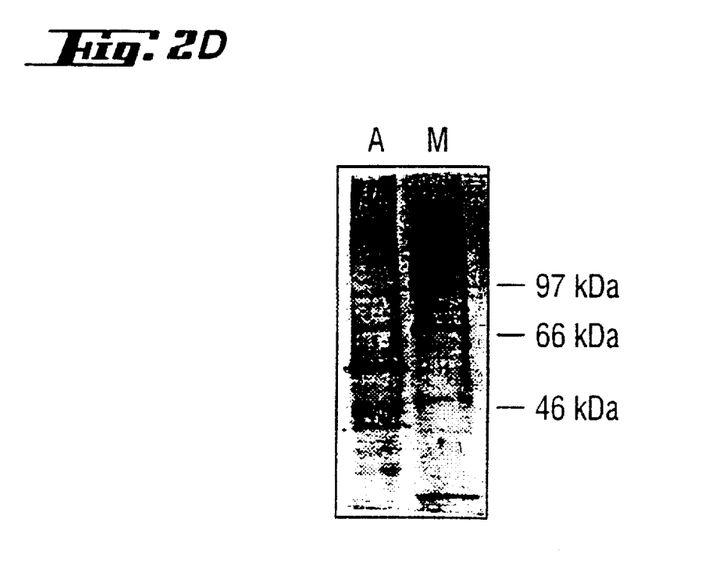

Example 8
SDS-polyacrylamide Gel Electrophoresis (Carried Out for FIGS. 1B, 2B and 2D)

SDS-polyacrylamide (acrylamide:bisacrylamide 30:0.8) gels (5% acrylamide in the spacer and 7.5% acrylamide in the resolving gel) were prepared as described by Laemmli, U.K. (1970) Nature 227, 680–685 using a Mini-protean II gel appliance (Bio-Rad No. 125BR). The appropriate quantities of protein were either fractionated directly on the gel or, before loading the gel, precipitated by adding 1 volume of 20% TCA followed by a centrifugation at 13,000 g and 4° C. for 30 minutes. The resulting precipitate was washed with acetone, dissolved in 10 µl of sample buffer (50 mM tris-HCl, pH 6.8, 1% (w/v) SDS, 100 mM DTT, 8% (v/v) glycerol, 0.025% (w/v) bromophenol blue) and fractionated by gel electrophoresis. The resulting gel was fixed and stained. The silver staining was performed as described by Oakley, B. R. et al. (1980) Anal. Biochem. 105, 361–363. The Commassie Brilliant Blue staining was carried out as described by Merryl, C. R. (1990) Meth. Enzymol. 182, 477–488.

Example 9
Preparing RNA Substrates

The 5'-capped RNA substrates (L3($A_{30}$), L3($A_{30}$)$X_{15}$, L3($A_{30}$)$X_{49}$ and L3($A_{30}$)$X_{164}$) were synthesized by in-vitro transcription using T3 RNA polymerase (Promega No. P208C) and the plasmid pT3L3($A_{30}$) (Åström, J. et al. (1991) EMBO J. 10(10), 3067–3071) as the DNA template, which was digested with NsiI, Hinc II, Eco RI and Pvu II. The RNA substrates ML ($G_{30}$), ML($C_{32}$) and ML($U_{30}$) were prepared as described in Åström, J. et al. (1991), as above. The RNA substrates were labeled either overall or on their homopolymeric tails by incorporating radioactively labeled mononucleotides during the in-vitro transcription (see Åström, J. (1991), above, Åström, J. et al. (1992), above). The specific radioactivities of the incorporated radioactive mononucleotides were 40 Ci/mmol in the case of the transcription mixture for the overall labeling or 4 Ci/mmol in the case of the transcription mixture for the tail labeling. Transcribed RNA was purified as described by Moore, C. L. & Sharp, P. A. (1985) Cell, 41, 845–855.

Example 10
In-vitro Deadenylation

The test conditions for the in-vitro deadenylation were as follows: 1 mM $MgCl_2$, 2.5% (w/v) poly(vinyl alcohol) (Sigma P-8136, Mw 10,000), 100 mM KCl, 0.15 Unit RNAguard, from 5 to 20 fmol of RNA substrate, from 20 to 48% (v/v) buffer (20 mM HEPES (KOH), 0.2 mM EDTA, 0.5 mM DTT, 25% glycerol, pH 7) and the appropriate protein fraction (Åström, J. et al. (1992), see above). The reaction volume was 15 or 25 µl and the incubations were carried out at 30° C. The reactions were then terminated and RNA was purified as described in Moore, C. L. & Sharpe, P. A. (1985), see above. The RNA was analyzed by electrophoresis in 10% polyacrylamide (19:1 acrylamide/bisacrylamide)—7 M urea gels, followed by autoradiography of the resulting gels.

Example 11
2D-thin Layer Chromatography

The two-dimensional (2D thin layer chromatography) was carried out on PEI-Cellulose F plates (Merck No. 5579) in accordance with the method of Konarska, M. M. et al. (1985) Nature 313 (6003), 552–557. The products released in the deadenylation reactions were analyzed by two-dimensional thin layer chromatography (2D TLC) carried out in a chamber. The first mobile solvent (I) was isobutyric acid/concentrated $NH_4OH/H_2O$; 577/38/385 (v/v), and the second mobile solvent (II) was saturated $(NH_4)_2SO_4$/1 M sodium acetate/isopropanol; 80/18/12 (v/v). After the first fractionation, the plates were dried at room temperature for 8 hours in order to evaporate off the isobutyric acid. 5'-AMP (Sigma A-1752), 2'-AMP (Sigma A-9396) and 3'-AMP (Sigma A-0386) were used as markers. The positions of the markers were determined using UV light (mineral light lamp UVG-54, Ultra Violet Prod. Inc.). The radioactive molecules were determined by subjecting the resulting PEI-Cellulose F plate to autoradiography.

Example 12
1D TLC and Quantification of the Nuclease Activity

The deadenylation activity was quantified as follows: L3($A_{30}$) RNA substrate, labeled with [$\alpha^{32}$P]ATP, was incubated in an in-vitro deadenylation reaction. The reaction products were analyzed by 1D TLC using mobile solvent III (0.75 M $K_2HPO_4$, pH 3.5 ($H_3PO_4$)). The resulting PEI-Cellulose F plate was dried and scanned in a 400 S Phosphorimager (Molecular Dynamics). The fractions containing released [$\alpha^{32}$P]AMP were determined. The quantity, in mol, of released AMP was calculated on the basis of the known specific activity of [$\alpha^{32}$P]AMP in the RNA substrate. One unit of deadenylation activity corresponds to the release of 1 pmol of AMP/minute.

Example 13
Conditions for the in-vitro Deadenylation

The conditions for measuring poly(A) deadenylation activity in accordance with the above-described deadenylation test were determined using Poly(A) Sepharose fractions as the enzyme source and poly(A) tail-labeled L3($A_{30}$) RNA as the substrate. The activity was measured in terms of the release of the mononucleotides in the 1D TLC test (see above). The requirement of monovalent (potassium and sodium) and divalent (magnesium, manganese, zinc and calcium) ions for this was investigated.

It was found that divalent cations are not required for the deadenylation activity and that the optimum monovalent cation concentration is approx. 100 mM. It was also found that the activity is higher in the presence of potassium ions than in the presence of sodium ions. It was also found that spermidine had no influence on the activity.

It was furthermore found that magnesium ions are the preferred divalent ion and that the optimum concentration is 1 mM. It was furthermore found that manganese, zinc and calcium ions can replace magnesium ions to a certain degree. In the presence of 1 mM $Mn^{2+}$, $Zn^{2+}$ and $Ca^{2+}$, the activity decreases by 17%, 2% and 0.7%, respectively, as compared with the activity in the presence of $Mg^{2+}$.

Investigations carried out with regard to the pH dependency showed that the activity is highest at approx. pH 7.

Example 14
Substrate Specificity

Figure 3:
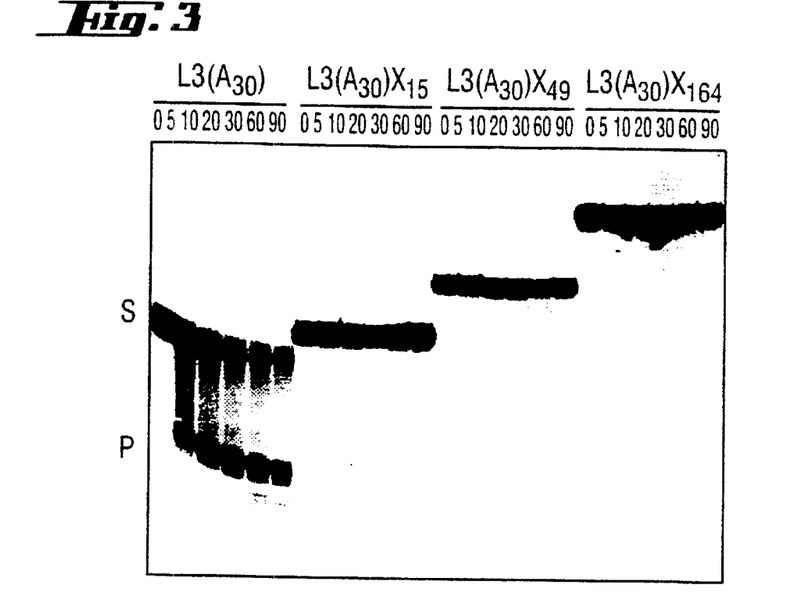

The RNA substrate specificity of the activity was investigated in two experiments. In a first experiment, the RNA substrates L3($A_{30}$), ML45($U_{30}$), ML40($C_{32}$) and ML43 ($G_{30}$), whose homopolymeric tails had been radioactively labeled, were incubated in an in-vitro deadenylation test (see above). The release of radioactive mononucleotides was measured in the 1D TLC test (see above). The measurement results were used to calculate the Km and Vmax values for each RNA substrate using the Lineweaver-Burke plot (see Table II). In a second experiment, the substrate specificity was measured by incubating RNA substrates containing internal poly(A) segments, followed by plasmid-encoded RNA sequences of increasing length, with Poly(A) Sepharose fractions in an in-vitro deadenylation test. It was found that the RNA substrates L3($A_{30}$)$X_{15}$, L3($A_{30}$)$X_{49}$ and L3($A_{30}$)$X_{164}$ were completely resistant to degradation, in contrast to the RNA substrate L3(A$_{30}$) (see FIG. 3). It follows from this that RNA tails composed of adenosine residues are the preferred substrate and that only 3' end-located poly(A) tails are effectively degraded.

Example 15
Determining the Mononucleotide which is Released

Figure 4:
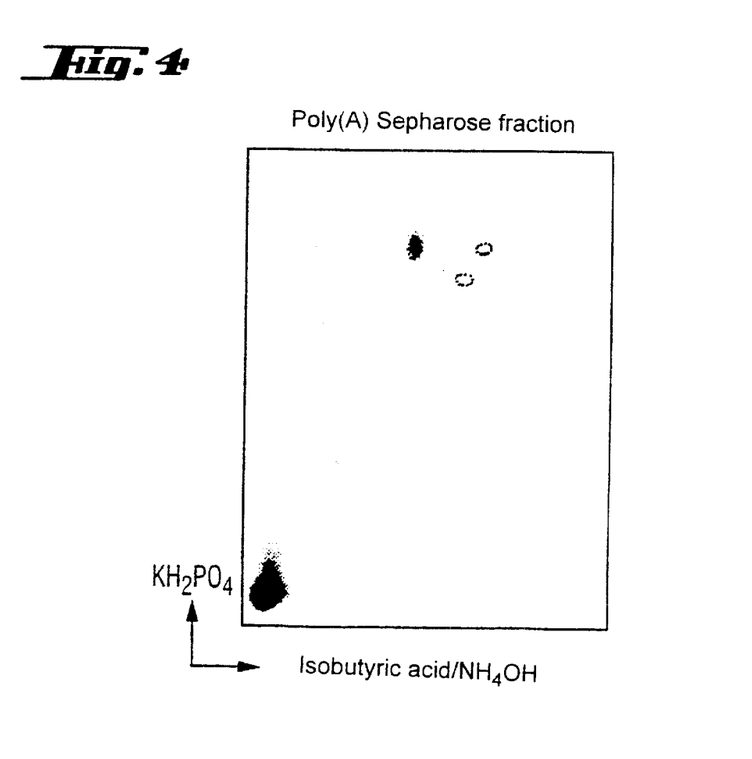

The mononucleotide reaction product which is released was determined by means of 2D TLC. For this, the Poly(A) Sepharose fraction was incubated, in an in-vitro deadenylation test, with L3(A$_{30}$) RNA substrate which had been labeled with [α$^{32}$P]AMP during the in-vitro transcription. After 20 minutes, the reaction products were analyzed by 2D TLC using unlabeled 2'-AMP, 3'-AMP and 5'-AMP as markers. This showed (see FIG. 4) that 5'-AMP is released during the in-vitro deadenylation reaction enzyme.

Example 16
Kinetics of the Nuclease Activity

Figure 5A:
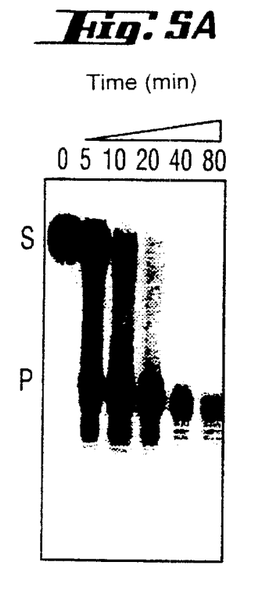
Figure 5B:
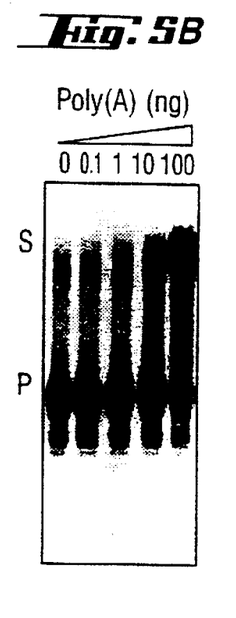
Figure 5C:
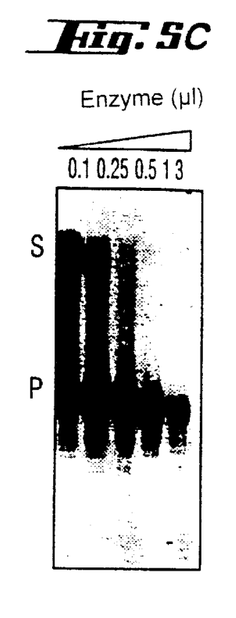

In order to determine whether the nuclease activity degrades RNA substrates in a progressive or distributive manner, the kinetics was first of all determined in an in-vitro deadenylation reaction in the presence of 0.5 μl of a Poly(A) Sepharose fraction and x fmol of L3(A$_{30}$) RNA substrate which had been labeled overall. FIG. 5A shows that completely degraded RNA accumulates before the entire RNA substrate has reacted. It follows from this that, under these conditions, the deadenylation reaction was completely finished after 20 minutes. In another reaction, the incubation was carried out for 20 minutes in the presence of an increasing quantity of poly(A). FIG. 5B shows that adding poly(A) inhibits the reaction and that both non-deadenylated and completely deadenylated RNA substrates were present in association with the highest measured concentration of added poly(A). In a third experiment, the quantity of nuclease activity was altered. The incubation time was 20 minutes. FIG. 5C shows that both non-deadenylated and deadenylated RNA substrates were present even in association with the smallest quantity of added nuclease activity. It follows from this that the exonuclease activity is highly progressive, i.e. the enzyme does not dissociate from the substrate until the adenosine tail has been completely degraded.

Figure 6A:
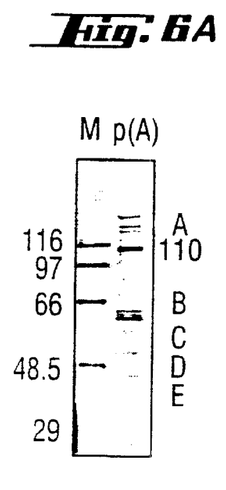
FIG. 6A:
SDS-PAGE for the refolding experiment in accordance with Dayle A. Hager and Richard R. Burgess, Anal. Biochem. (1980), 109, 76. The resulting gel was stained with silver. The numbers on the left-hand side indicate the molecular weights of the marker proteins in kDa. The resulting bands were excised, as indicated in FIG. 6A (A, 110, B, C, D and E).
Figure 6B:
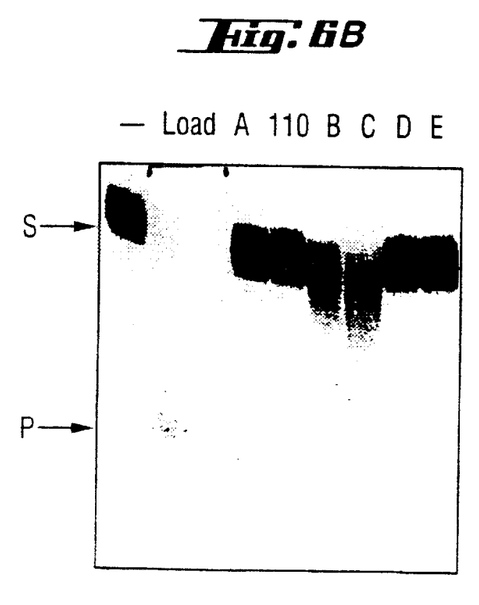
Figure 7:
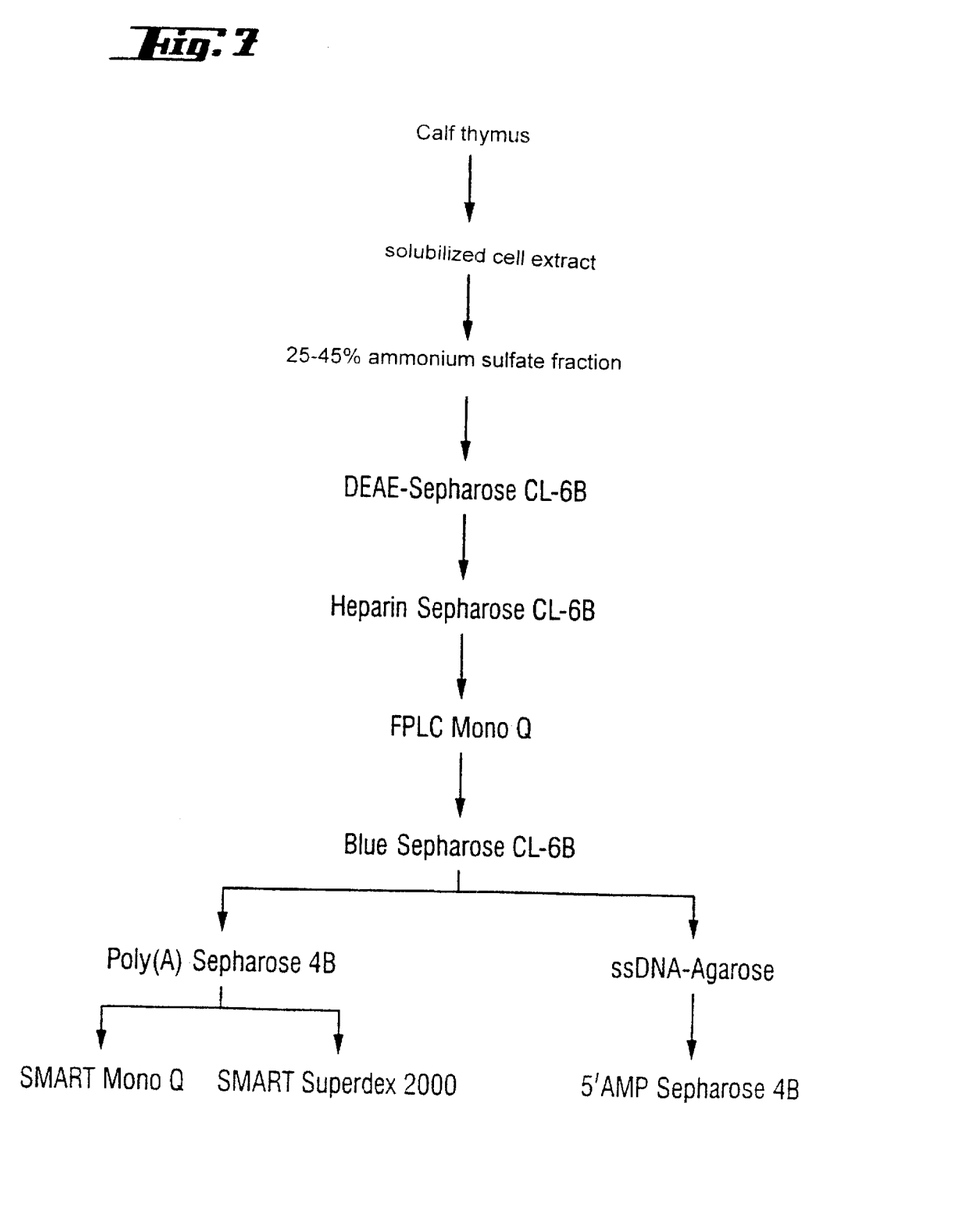
FIG. 7 shows the chromatographic steps involved in the process according to the invention.

Example 17
Refolding Experiment (FIG. 6)

The refolding experiments were carried out as described by Dayle et al. (see above) apart from the fact that the refolding took place on the gel overnight at 4 degrees centigrade. The active fractions on the Poly(A) Sepharose chromatography (Ex. 3) were used for these experiments.

What is claimed is:

1. A process for isolating a poly(A)-specific 3'-exonuclease comprising the following:
   (a) preparing a crude extract from animal or human cells;
   (b) precipitating protein present in the crude extract to obtain a precipitate;
   (c) subjecting the precipitate to chromatography on a weakly basic anion exchanger to obtain a first active fraction;
   (d) subjecting the first active fraction to affinity chromatography on heparin to obtain a second active fraction;
   (e) subjecting the second active fraction to chromatography on a strongly basic anion exchanger to obtain a third active fraction;
   (f) subjecting the third active fraction to affinity chromatography on a dye to obtain a fourth active fraction;
   (g) subjecting the fourth active fraction to poly(A)-affinity chromatography to obtain a fifth active fraction; and
   (h) subjecting the fifth active fraction to chromatography on a basic anion exchanger; wherein a poly(A)-specific 3'-exonuclease is isolated.

2. The process of claim 1, wherein the animal or human cells are thymus cells.

3. The process of claim 1, wherein the precipitation according to step (b) occurs in ammonium sulfate at approximately 45% saturation.

4. The process of claim 3, wherein the precipitation according to step (b) comprises the following:
   (1) precipitating protein present in the crude extract in ammonium sulfate at approximately 25% saturation, then
   (2) adding further ammonium sulfate such that approximately 45% saturation of ammonium sulfate is present in a supernatant.

5. The process of claim 1, wherein
   (1) the precipitate is obtained by precipitation using ammonium sulfate;
   (2) the first active fraction is obtained using chromatography on DEAE;
   (3) the third active fraction is obtained using chromatography on Mono Q;
   (4) the fourth active fraction is obtained using affinity chromatography on a blue dye; and
   (5) the fifth active fraction is subjected to chromatography on a strongly basic anion exchanger.

6. The process of claim 5, wherein
   (1) the fourth active fraction is obtained using chromatography on Blue Sepharose; and
   (2) the fifth active fraction is subjected to chromatography on Mono Q.

7. The process of claim 1, wherein
   (1) the first active fraction is eluted at an approximate 0.17 M concentration of a salt;
   (2) the second active fraction is eluted at an approximate 1.0 M concentration of a salt;
   (3) the third active fraction is eluted at an approximate 10% concentration of a 1.0 M concentration of a salt;
   (4) the fourth active fraction is eluted at an approximate 1.0 M concentration of a salt; or
   (5) the fifth active fraction is eluted at an approximate 0.35–0.55 M concentration of a salt.

8. A process for isolating a poly(A)-specific 3'-endonuclease comprising the following:
   (a) preparing a crude extract from animal or human cells;
   (b) precipitating protein present in the crude extract to obtain a precipitate;
   (c) subjecting the precipitate to chromatography on a weakly basic anion exchanger to obtain a first active fraction;
   (d) subjecting the first active fraction to affinity chromatography on heparin to obtain a second active fraction;
   (e) subjecting the second active fraction to chromatography on a strongly basic anion exchanger to obtain a third active fraction;
   (f) subjecting the third active fraction to affinity chromatography on a dye to obtain a fourth active fraction;
   (g) subjecting the fourth active fraction to poly(A)-affinity chromatography to a obtain a fifth active fraction;
   (h) subjecting the fifth active fraction to gel filtration to obtain a sixth active fraction; and (i) subjecting the sixth active fraction to chromatography on a basic anion exchanger, wherein a poly(A)-specific 3'-exonuclease is isolated.

9. The process of claim 8, wherein the animal or human cells are thymus cells.

10. The process of claim 8, wherein
  (1) the precipitate is obtained by precipitation using ammonium sulfate;
  (2) the first active fraction is obtained using chromatography on DEAE;
  (3) the third active fraction is obtained using chromatography on Mono Q;
  (4) the fourth active fraction is obtained using chromatography on a blue dye; and
  (5) the sixth active fraction is subjected to chromatography on a strongly basic anion exchanger.

11. The process of claim 10, wherein
  (1) the fourth active fraction is obtained using chromatography on Blue Sepharose; and
  (2) the sixth active fraction is subjected to chromatography on Mono Q.

12. The process of claim 8, wherein the precipitation according to step (b) occurs in ammonium sulfate at approximately 45% saturation.

13. The process of claim 12, wherein
  (1) the first active fraction is eluted at an approximate 0.17 M concentration of
  (2) the second active fraction is eluted at an approximate 1.0 M concentration of a salt;
  (3) the third active fraction is eluted at an approximate 10% concentration of a 1.0 M concentration of a salt;
  (4) the fourth active fraction is eluted at an approximate 1.0 M concentration of a salt;
  (5) the fifth active fraction is eluted at an approximate 0.35–0.55 M concentration of a salt; or
  (6) the sixth active fraction is subjected to chromatography on a basic anion exchanger using approximate 0.17 M concentration of a salt.

14. A process for isolating a poly(A)-specific 3'-endonuclease comprising the following:
  (a) preparing a crude extract from animal or human cells;
  (b) precipitating protein present in the crude extract to obtain a precipitate;
  (c) subjecting the precipitate to chromatography on a weakly basic anion exchanger to obtain a first active fraction;
  (d) subjecting the first active fraction to affinity chromatography on heparin to obtain a second active fraction;
  (e) subjecting the second active fraction to chromatography on a strongly basic anion exchanger to obtain a third active fraction;
  (f) subjecting the third active fraction to affinity chromatography on a dye to obtain a fourth active fraction;
  (g) subjecting the fourth active fraction to two rounds of affinity chromatography to obtain a fifth active fraction;
  (h) subjecting the fifth active fraction to poly(A)-affinity chromatography to obtain a sixth active fraction; and
  (i) subjecting the sixth active fraction to chromatography on a basic anion exchanger, wherein a poly(A)-specific 3'-exonuclease is isolated.

15. The process of claim 14, wherein the animal or human cells are thymus cells.

16. The process of claim 14, wherein
  (1) the precipitate is obtained by precipitation using ammonium sulfate;
  (2) the first active fraction is obtained using chromatography on DEAE;
  (3) the third active fraction is obtained using chromatography on Mono Q;
  (4) the fourth active fraction is obtained using chromatography on a blue dye;
  (5) the fifth active fraction is obtained using ssDNA Agarose following by 5' AMP chromatography; and
  (6) the sixth active fraction is subjected to chromatography on a strongly basic anion exchanger.

17. The process of claim 16, wherein
  (1) the fourth active fraction is obtained using chromatography on Blue Sepharose; and
  (2) the sixth active fraction is subjected to chromatography on Mono Q.

18. The process of claim 14, wherein the precipitation according to step (b) occurs in ammonium sulfate at approximately 45% saturation.

19. The process of claim 18, wherein
  (1) the first active fraction is eluted at an approximate 0.17 M concentration of a salt;
  (2) the second active fraction is eluted at an approximate 1.0 M concentration of a salt;
  (3) the third active fraction is eluted at an approximate 10% concentration of a 1.0 M concentration of a salt;
  (4) the fourth active fraction is eluted at an approximate 1.0 M concentration of a salt;
  (5) the fifth active fraction is eluted at an approximate 2.0 M concentration of a salt;
  (6) the sixth active fraction is eluted at an approximate 0.35–0.55 M concentration of a salt; or
  (7) the sixth active fraction is subjected to chromatography on a basic anion exchanger using an approximate 0.17 M concentration of a salt.

20. A composition comprising the poly(A)-specific 3'-exonuclease isolated by the process of claim 1.

21. A formulation comprising the composition of claim 20 and a pharmaceutically acceptable additive and/or adjuvant.

22. A process comprising combining the composition of claim 20 and a pharmaceutically acceptable adjuvant and/or additive.

23. A composition comprising a poly(A) specific 3'-exonuclease, obtainable from calf thymus, that interacts strongly with Heparin Sepharose, catalyses degradation of poly(A)nucleotides at the 3' end of mRNAs in a processive manner, has a molecular weight of 50 kDa under denaturing conditions and a molecular weight of 180–220 kDa under native conditions, is active in the presence of 1 mM $Mn^{2+}$ ions and is not stimulated by spermidine.

* * * * *